US 6,700,020 B2

(12) United States Patent
Pabst et al.

(10) Patent No.: US 6,700,020 B2
(45) Date of Patent: Mar. 2, 2004

(54) SEMI-CONTINUOUS METHOD FOR PRODUCING 4,4'-DIHYDROXYDIPHENYL SULFONE

(75) Inventors: Gunther Pabst, Mannheim (DE); Jürgen Kast, Böhl-Iggelheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/257,328

(22) PCT Filed: Apr. 10, 2001

(86) PCT No.: PCT/EP01/04081
§ 371 (c)(1),
(2), (4) Date: Oct. 10, 2002

(87) PCT Pub. No.: WO01/79163
PCT Pub. Date: Oct. 25, 2001

(65) Prior Publication Data
US 2003/0149308 A1 Aug. 7, 2003

(30) Foreign Application Priority Data
Apr. 14, 2000 (DE) .......................... 100 18 580

(51) Int. Cl.⁷ .............................. C07C 315/00
(52) U.S. Cl. ..................... 568/33; 568/28; 568/32
(58) Field of Search ................ 568/28, 32, 33

(56) References Cited

U.S. PATENT DOCUMENTS
3,297,766 A 1/1967 Bradley et al.

FOREIGN PATENT DOCUMENTS
EP 220 004 4/1987
WO 92/02493 2/1992

OTHER PUBLICATIONS
JP/50/106/936 Abstract.
CN 87,100,796 Abstract.
Jrl.Chem.Soc., Hinkel et al.

Primary Examiner—J. Parsa
(74) Attorney, Agent, or Firm—Keil & Weinkauf

(57) ABSTRACT

A semicontinuous process is provided for the preparation of 4,4'-dihydroxydiphenyl sulfone, comprising the following steps:
(a) reaction of phenol with a sulfonating agent,
(b) suspension of the resulting crude product in water heated to at least 40° C., which is free of inert organic solvents and can contain residual amounts of unreacted phenol, and filtration of the product, and
(c) recycling of the resulting educt-containing and/or product-containing waste streams into the preparative process, wherein, in carrying out step (b), the crude product and water are used in a weight ratio of 85:15 to 55:45.

9 Claims, No Drawings

SEMI-CONTINUOUS METHOD FOR PRODUCING 4,4'-DIHYDROXYDIPHENYL SULFONE

The present invention relates to an improved semicontinuous process for the preparation of 4,4'-dihydroxydiphenyl sulfone, comprising the following steps:

(a) reaction of phenol with a sulfonating agent, (b) suspension of the resulting crude product in water heated to at least 40° C., which is free of inert organic solvents and can contain residual amounts of unreacted phenol, and filtration of the product, and (c) recycling of the resulting educt-containing and/or product-containing waste streams into the preparative process.

4,4'-Dihydroxydiphenyl sulfone ("4,4'-bisphenol S") is of great economic value inter alia as an auxiliary substance for electroplating, as a raw material for the manufacture of condensation resins, for example to be used as leather tanning agents, and for the manufacture of fibers and especially plastics such as polyether sulfones. As the properties of polymers prepared from 4,4'-dihydroxydiphenyl sulfone are highly dependent on the degree of purity and the isomer ratio of the monomers used, it is desirable to have selective processes for the synthesis of 4,4'-dihydroxydiphenyl sulfone. It is also desirable, for economic and ecological reasons, to have synthetic processes with minimal waste streams or none at all.

Synthetic processes which make use of combustible inert organic solvents, such as methanol, ethanol, o-dichlorobenzene or toluene, in the isolation of 4,4'-dihydroxydiphenyl sulfone from the reaction mixture, for example the processes described in JP-A 50/106 937, CN-A 87/100 796, EP-A 220 004 or WO 92/02493, are likewise unacceptable for ecological and safety reasons.

U.S. Pat. No. 3,297,766 has disclosed a semicontinuous process for the preparation of 4,4'-dihydroxydiphenyl sulfone wherein sulfuric acid is reacted with phenol at 180–188° C. with continuous distillation of the water of reaction, the reaction mixture is then cooled to 55–75° C. and the solid which has precipitated out is filtered off and washed with water to give a mixture of 4,4'-and 2,4'-dihydroxydiphenyl sulfone. The waste streams from the filtration and rinsing, and the phenol discharged during distillation of the water of reaction, are fed back into the next cycle of the preparative process.

JP-A 50/106 936 describes the preparation of 4,4'-dihydroxydiphenyl sulfone by reacting phenol with a sulfonating agent, such as sulfuric acid, at 180–200° C. and crystallizing out and separating off the 4,4'-dihydroxydiphenyl sulfone. The latter is isolated by dissolving or dispersing the crude reaction product in 3 to 8% by weight aqueous phenol solution and crystallizing out and separating off the 4,4'-dihydroxydiphenyl sulfone with or without cooling. If there is still a relatively large amount of unreacted phenol in the reaction product, it is only possible to work with the addition of pure water. 1 to 5 parts by weight of aqueous phenol solution are used per part by weight of reaction product. The solution separated off, which contains phenol and water, can be re-used in a subsequent reaction cycle. According to the Example in JP-A 50/106 936, treatment of the reaction product with 8% by weight aqueous phenol solution at 75° C., cooling to 40° C. and centrifugation of the 4,4'-dihydroxydiphenyl sulfone which has precipitated out gives an isomeric purity of 98.7%.

Although the process of JP-A 50/106 936 provides the desired product in high isomeric purity, it has the disadvantage of working with large amounts of aqueous treatment solution for isolation from the reaction mixture. These amounts on the one hand require sizeable and hence expensive apparatuses and on the other hand reduce the yield. Furthermore, the presence of large amounts of phenol in the isolation of the product has the disadvantage that the phenol can easily remain stuck to the product as an impurity by forming adduct complexes therewith.

It is known that sulfonation reactions of phenol with sulfuric acid involve reversible equilibria which, with further phenol, proceed via phenol-2-sulfonic acid and phenol-4-sulfonic acid to give 2,4'- and 4,4'-dihydroxydiphenyl sulfone. The isomerization equilibrium which exists between 2,4'- and 4,4'-dihydroxydiphenyl sulfone favors the thermodynamically more stable 4,4' isomer. However, the isomerization is kinetically inhibited and a catalyst, for example phenol-4-sulfonic acid, is usually necessary for the equilibrium to be reached within a period acceptable in terms of process engineering. The isomerization equilibrium can also be shifted in favor of the 4,4' isomer by selectively withdrawing it. Furthermore, if the phenol is present in less than the stoichiometric amount, trimers, such as 2,4',4"-trihydroxytriphenyl disulfone, and higher phenolsulfonic acid oligomers can be formed.

It is an object of the present invention to provide a preparative process for 4,4'-dihydroxydiphenyl sulfone which is free of inert organic solvents in the steps involving the reaction and the isolation of the product from the reaction mixture, in which the waste streams can be recycled into the preparative process, which yields the desired product in high isomeric purity and high yield, even without downstream purification operations, and which, in the isolation of the product from the reaction mixture, involves the smallest possible amounts of treatment solution, the latter being substantially free of unreacted phenol.

We have found that this object is achieved by the semicontinuous process for the preparation of 4,4'-dihydroxydiphenyl sulfone defined at the outset, wherein, in carrying out step (b), the crude product and water are used in a weight ratio of 85:15 to 55:45, preferably 75:25 to 60:40.

The hot water used to suspend the reaction mixture is free of inert organic solvents, especially water-miscible solvents such as methanol, ethanol, isopropanol or acetone, or, if appropriate, halogenated hydrocarbons such as toluene, chlorobenzene or dichlorobenzenes. The residual amounts of unreacted phenol which can be dissolved out of the reaction mixture in the suspension step, or which may already be present to a small extent in the water used, if the latter originates from the previous cycle of the preparative process and has been produced by distillation of the mother liquor from step (b) of said cycle, can be up to a maximum of 2.5% by weight, particularly 0.05 to 1.5% by weight and very particularly 0.1 to 1.0% by weight, based in each case on the amount of water used.

In one preferred embodiment, the water added for treating the reaction mixture in step (b) is at a temperature of 80° C. to 100° C. Particularly good results are achieved with water at 90° C. to 100° C. In principle, it is also possible to work at temperatures above 100° C., for example at 100° C. to 130° C., if the treatment with water is carried out in a closed apparatus under superatmospheric pressure. The treatment water can also be added in the form of steam. The duration of the treatment with water is not critical and as a rule is 5 minutes to 5 hours. The treatment with water is normally accompanied by thorough mechanical mixing, for example by stirring.

In another preferred embodiment, the suspension of the crude product in water and the filtration of the product, in step (b), are carried out at approximately the same temperature. Approximately the same temperature conventionally means working in a temperature range of approx. 10° C., especially approx. 5° C. This embodiment avoids cooling of the suspension, which would result in the crystallization of dissolved constituents.

The suspension ("slurrying") and the filtration can be carried out by the techniques and with the apparatuses conventionally used for this purpose, for example with stirred tanks, mixers or kneaders for the suspension, and with suction filters or centrifuges for the filtration.

In another preferred embodiment, the product filtered off in step (b) is rinsed with water heated to at least 40° C., preferably 80° C. to 100° C. and especially 90° C. to 100° C. The amount of water used for rinsing should be as small as possible and is normally at most 100%, preferably at most 85%, of the water used to suspend the reaction mixture.

Step (b) is very particularly preferably implemented in such a way that the suspension of the crude product in water and the filtration of the product are carried out at approximately the same temperature in the range 80° C. to 100° C., especially 90° C. to 100° C., and the filtered product is rinsed with at most 100%, especially at most 85%, of the water used to suspend the reaction mixture, which is also at approximately the same temperature as in the suspension and filtration operations.

One advantage of the process according to the invention is that the product prepared according to the abovementioned measures in step (b) normally already has an average purity of >96%, especially >97.5%, and an average isomeric purity of >98%, especially >98.4%. This high purity and isomeric purity are achieved by the fact that, in contrast to all the processes known hitherto, the already very pure crude crystals of 4,4'-dihydroxydiphenyl sulfone formed during the reaction in step (a) are not destroyed, but are freed by the hot treatment water of the 2,4'-dihydroxydiphenyl sulfone, which is more soluble in the mother liquor and accumulates therein. Although the high selectivity of the procedure causes a loss of yield due to the solubility of 4,4'-dihydroxydiphenyl sulfone, this loss is ultimately compensated by the recycling of the waste streams according to step (c) and the semicontinuous procedure.

Another advantage of the process according to the invention is that, after distillation of the water, the mother liquor from step (b), containing mainly 2,4'-dihydroxydiphenyl sulfone, is re-used in step (a) at the beginning of the next cycle of the preparative process with skilful utilization of the chemical equilibrium. The residue of the mother liquor is thereby converted to phenolsulfonic acid. The water distilled off can likewise be re-used in step (b) of the next cycle.

The process according to the invention is also distinguished by a high overall yield generally exceeding 90%, especially of 92% or more, based in each case on the phenol used.

The 4,4'-dihydroxydiphenyl sulfone prepared by the process according to the invention is also distinguished by its good crystallization behavior, i.e. the crystals obtained are large and well formed and have a low dust content, so they can be handled and metered easily.

The sulfonating agent used in step (a) is preferably concentrated sulfuric acid, oleum ("fuming" sulfuric acid) or sulfur trioxide ("sulfuric anhydride"). It is particularly preferable to use concentrated sulfuric acid with a content of approx. 70 to 100% by weight, for example the approx. 96% by weight sulfuric acid available commercially.

Step (a) of the process according to the invention can be carried out as described below.

The phenol and the sulfonating agent can be combined and then brought to the reaction temperature, although the phenol can also be metered in portions or continuously throughout the reaction, especially after the heating phase.

The reaction temperature is conventionally 140° C. to 230° C., particularly 150° C. to 200° C. and very particularly 160° C. to 175° C. If the reaction temperature is below 165° C., it is advisable to work under reduced pressure to ensure that the phenol boils.

In the overall reaction in step (a), the molar ratio of phenol to sulfonating agent, for example sulfuric acid, is normally 1.6:1 to 25:1, preferably 1.8:1 to 10:1 and particularly preferably 1.9:1 to 2.5:1.

The water formed in the sulfonation of phenol with sulfuric acid or phenolsulfonic acid can be continuously distilled azeotropically out of the reaction by means of excess phenol present in the reaction mixture, and the phenol can be recycled into the reactor after separation of the water phase. After the azeotropic distillation ("extraction") of usually at least 50% but preferably 90 to 100% of the theoretical amount of water formed, no more phenol is generally recycled into the reaction, but the phenol is gradually distilled off, expediently at 160° C. to 200° C. The unreacted phenol is re-used in the next cycle of the preparative process.

In one preferred embodiment, firstly phenol is extensively reacted with the sulfonating agent in step (a) to give phenolsulfonic acid, any water of reaction thereby formed is removed by distillation, the phenolsulfonic acid is then reacted with more phenol to give dihydroxydiphenyl sulfone and the water of reaction thereby formed is again removed by distillation.

This is generally followed by an isomerization phase of the reaction mixture at a temperature conventionally of 140° C. to 180° C., especially 150° C. to 170° C., and for an isomerization time normally of 0.1 to 10 hours, especially 1 to 4 hours. During this isomerization phase, the equilibrium shifts in favor of 4,4'-dihydroxydiphenyl sulfone and the amount of 2,4'-dihydroxydiphenyl sulfone decreases. The isomerization is normally catalyzed by small amounts of phenolsulfonic acid, which conventionally is still present in small amounts in the reaction mixture, especially when working with a slight stoichiometric excess of sulfonating agent.

In one preferred embodiment, excess phenol is virtually completely removed by distillation after the reaction of step (a) but generally before an isomerization phase.

Before the hot treatment water is added according to step (b), the reaction mixture is conventionally cooled to temperatures below 130° C.

The recycling of the resulting educt-containing and/or product-containing waste streams into the preparative process according to step (c), i.e. after the distillation of water into the next cycle of the preparative process, preferably takes place in a closed system, i.e. completely, based on the phenol used, the phenolsulfonic acid intermediate and the dihydroxydiphenyl sulfones. The recycling of phenol distilled off azeotropically with water in step (a) and from the mother liquor in step (b), which remains dissolved in the condensate and cannot be obtained as a separate phase by conventional phase separation, usually turns out to be uneconomic—especially since these amounts of phenol are negligibly small—and can therefore be omitted.

Semicontinuous procedure is to be understood as meaning the multiple repetition ("cyclic procedure") of noncontinuous process steps, with the recycling of process streams. The number of cycles for which the semicontinuous process according to the invention can run is basically unlimited. Conventionally, after the third or fourth cycle, the equilibrium has reached a quasi-stationary state as regards the characteristics of the recycled waste streams and the purity and conversion data of the overall reaction. Remarkably, no impurities or by-products accumulate, as far as can be determined after approx. 10 cycles.

The 4,4'-dihydroxydiphenyl sulfone obtained in step (b) can be further purified by conventional recrystallization. This is preferably effected from a water/acetone mixture generally having a volume ratio of 50:50 to 97:3, especially 80:20 to 95:5. Instead of acetone, however, it is also possible to use other water-soluble or water-miscible organic solvents, e.g. aliphatic alcohols having from 1 to 3 C atoms, such as methanol, ethanol, n-propanol or isopropanol, dimethyl sulfoxide, dimethylformamide, dioxane, ethylene glycol, propylene glycol or higher ethylene or propylene glycols having up to 3 glycol units, in conventional mixing ratios with water. The concomitant use of activated charcoal in the recrystallization is also often advantageous, the resulting pure product generally having an isomeric purity of at least 99.7% in respect of 4,4'-dihydroxydiphenyl sulfone.

The following Example will illustrate the present invention without implying a limitation.

EXAMPLE

Step (a)

512 g of mother liquor from step (b) of the previous cycle (proportion of non-volatile constituents: 32.2% by weight) were concentrated by distillation of the water under reduced pressure at 110° C. for 2.5 hours. 346 g (3.7 mol) of phenol and then 437 g (4.3 mol) of 96% by weight sulfuric acid were metered in for this purpose. The mixture was subsequently stirred for 1 hour at 160° C. The pressure was then adjusted to 150 mbar and the water of reaction formed was extracted over 3 hours.

45.4 g of residual phenol from the previous cycle (proportion of non-volatile constituents: 72.5% by weight, 0.4 mol) and 472 g (5.0 mol) of fresh phenol were metered into the reaction mixture at 165° C. under atmospheric pressure. The pressure was reduced to 300 mbar and the water of reaction was extracted over 6 hours. The excess phenol was then distilled off as completely as possible. A total of 180 g of phenol-containing water of reaction (proportion of non-volatile constituents: 9.8% by weight, 0.2 mol of phenol) and 62 g of aqueous residual phenol (proportion of non-volatile constituents: 74% by weight, 0.5 mol of phenol) were formed.

The reaction mixture was ventilated with nitrogen and the temperature was gradually lowered from 165° C. to 140° C. over one hour. Isomerization was then carried out for a further 3 hours at this temperature.

Step (b)

583 g of water at 90° C., obtained by distillation from the mother liquor in step (b) of the previous cycle, were added to the reaction mixture (1223 g) at 100° C. and the resulting mixture was slurried by stirring for 15 minutes at 90–95° C. The suspension was then filtered at 90° C. and rinsed with three times 160 g of water at 90° C. to give 1120 g of crystals (4.5 mol of dihydroxydiphenyl sulfone, based on freshly introduced phenol).

Recrystallization

The crystals obtained were recrystallized at 80° C. from 7200 ml of a mixture of water and acetone in a volume ratio of 90:10, with the concomitant use of activated charcoal. This was done by dissolving the crystals at 80° C., adding 3.2 g of commercially available activated charcoal and stirring at this temperature. Clarification through a heated pressure filter produced a colorless solution. After cooling to 25° C., the colorless crystals were filtered off with suction and washed with twice 200 g of water to give 1031 g of pure colorless crystals (4.1 mol, 95% based on freshly introduced phenol).

After the process had been run for 10 cycles analogously to the procedure described above, the overall yield of 4,4'-dihydroxydiphenyl sulfone was 92%, based on the phenol used, and the average purity was 98.4% (product from step (b)) or, after recrystallization, 99.7%.

We claim:

1. A semicontinuous process for the preparation of 4,4'-dihydroxydiphenyl sulfone, comprising the following steps:

(a) reaction of phenol with a sulfonating agent, (b) suspension of the resulting crude product in water heated to at least 40° C., which is free of inert organic solvents and can contain residual amounts of unreacted phenol, and filtration of the product, and (c) recycling of the resulting educt-containing and/or product-containing waste streams into the preparative process, wherein, in carrying out step (b), the crude product and water are used in a weight ratio of 85:15 to 55:45.

2. A process as claimed in claim 1 wherein, in step (b), the residual amounts of unreacted phenol in the water are at most 2.5% by weight.

3. A process as claimed in claim 1 wherein the water in step (b) is at a temperature of 80° C. to 100° C.

4. A process as claimed in claim 1 wherein, in step (b), the suspension of the crude product in water and the filtration of the product are carried out at approximately the same temperature.

5. A process as claimed in claim 1 wherein, in step (b), the product filtered off is rinsed with water heated to at least 40° C.

6. A process as claimed in claim 1 wherein the sulfonating agent used in step (a) is concentrated sulfuric acid, oleum or sulfur trioxide.

7. A process as claimed in claim 1 wherein, in step (a), firstly phenol is extensively reacted with the sulfonating agent to give phenolsulfonic acid, any water of reaction thereby formed is removed by distillation, the phenolsulfonic acid is then reacted with more phenol to give dihydroxydiphenyl sulfone and the water of reaction thereby formed is again removed by distillation.

8. A process as claimed in claim 1 wherein (a) excess phenol is virtually completely removed by distillation after the reaction of step.

9. A process as claimed in claim 1 wherein the 4,4'-dihydroxydiphenyl sulfone obtained in step (b) is further purified by recrystallization from a water/acetone mixture.

* * * * *